(12) United States Patent
Merkel et al.

(10) Patent No.: US 9,139,510 B2
(45) Date of Patent: Sep. 22, 2015

(54) PROCESS FOR PREPARING AROMATIC AMINES

(75) Inventors: Michael Merkel, Düsseldorf (DE); Karl-Heinz Wilke, Moers (DE); Peter Lehner, Houston, TX (US); Andre Lago, Hamburg (DE); Erwin Dieterich, Köln (DE)

(73) Assignee: BAYER INTELLECTUAL PROPERTY GMBH, Monheim (DE)

( * ) Notice: Subject to any disclaimer, the term of this patent is extended or adjusted under 35 U.S.C. 154(b) by 68 days.

(21) Appl. No.: 13/978,479

(22) PCT Filed: Jan. 6, 2012

(86) PCT No.: PCT/EP2012/050161
§ 371 (c)(1),
(2), (4) Date: Dec. 6, 2013

(87) PCT Pub. No.: WO2012/095356
PCT Pub. Date: Jul. 19, 2012

(65) Prior Publication Data
US 2014/0128638 A1    May 8, 2014

(30) Foreign Application Priority Data
Jan. 11, 2011   (DE) .......................... 10 2011 002 497

(51) Int. Cl.
*C07C 209/00* (2006.01)
*C07C 209/36* (2006.01)

(52) U.S. Cl.
CPC .................................... *C07C 209/36* (2013.01)

(58) Field of Classification Search
CPC combination set(s) only.
See application file for complete search history.

(56) References Cited

U.S. PATENT DOCUMENTS

| | | | |
|---|---|---|---|
| 7,193,112 | B2 | 3/2007 | Lehner et al. |
| 2005/0080293 | A1 | 4/2005 | Lehner et al. |

FOREIGN PATENT DOCUMENTS

| | | |
|---|---|---|
| DE | 2849002 A1 | 5/1980 |
| EP | 1524259 A1 | 4/2005 |
| GB | 1452466 A | 10/1976 |

OTHER PUBLICATIONS

International Search Report for PCT/EP2012/050161 Mailed Mar. 27, 2012.

*Primary Examiner* — Clinton Brooks
(74) *Attorney, Agent, or Firm* — Miles & Stockbridge P.C.

(57) ABSTRACT

The invention relates to a process for the continuous preparation of aromatic amines by hydrogenation of the corresponding nitroaromatics in the presence of catalysts arranged in reaction spaces, in which an adiabatically operated reaction space RA is connected downstream of an isothermally operated reaction space RI and RA additionally also has a separate feed for the nitroaromatic to be hydrogenated, RI is fed with the nitroaromatic to be hydrogenated from the start to the end of the hydrogenation, and the product mixture emerging from RI is fed into RA from the start to the end of the hydrogenation, wherein RA can additionally be fed via the separate feed with the nitroaromatic to be hydrogenated.

6 Claims, No Drawings

PROCESS FOR PREPARING AROMATIC AMINES

CROSS REFERENCE TO RELATED APPLICATIONS

This application is a §371 National Stage Application of PCT/EP2012/050161, filed Jan. 6, 2012, which claims priority to European Application No. 10 2011 002 497.2, filed Jan. 11, 2011.

BACKGROUND OF THE INVENTION

1. Field of the Invention

The invention relates to a process for the continuous preparation of aromatic amines by hydrogenation of the corresponding nitroaromatics in the presence of catalysts arranged in reaction spaces, in which an adiabatically operated reaction space RA is connected downstream of an isothermally operated reaction space RI and RA additionally also has a separate feed for the nitroaromatic to be hydrogenated, RI is fed with the nitroaromatic to be hydrogenated from the start to the end of the hydrogenation, and the product mixture emerging from RI is fed into RA from the start to the end of the hydrogenation, wherein RA additionally is fed via the separate feed with the nitroaromatic to be hydrogenated.

2. Description of Related Art

Aromatic amines are important intermediate products which must be prepared inexpensively and in large amounts. Production installations for aromatic amines are therefore as a rule built for very high capacities. The hydrogenation of nitroaromatics is a highly exothermic reaction. The removal of the heat of reaction and its use for energy are therefore an important point in the preparation of nitroaromatics.

DE-OS-28 49 002 describes a process for the reduction of nitro compounds in the presence of palladium-containing multi-component supported catalysts of fixed position in cooled tube bundle reactors. The catalysts essentially comprise 1 g to 20 g of palladium, 1 g to 20 g of vanadium and 1 g to 20 g of lead per liter of $\alpha$-$Al_2O_3$. A disadvantage of the gas phase hydrogenations described in the patent literature mentioned is the low specific loading of the catalysts with the nitroaromatic to be hydrogenated. The loadings stated are only approx. 0.4 $kg_{nitroaromatic}/(1_{catalyst} \cdot h)$ to 0.5 $kg_{nitroaromatic}/(1_{catalyst} \cdot h)$. The loading in this context is defined as the amount of nitroaromatic in kg which is passed over the catalyst per liter of bulk catalyst (catalyst volumes here and in the following relate to the bulk volume) within one hour. An unsatisfactory space-time yield is associated with the low catalyst loading in large-scale industrial processes for the preparation of aromatic amines. The selectivities at the start of an operating period are furthermore significantly lower than towards the end, which leads to losses in yield and problems in the working up of the crude product.

In the process variant described in GB 1 452 466, the hydrogenation of nitroaromatics in thermostatically controlled tube bundle reactors is supplemented by a downstream adiabatically (i.e. without thermostatic control) operated reactor. Supported copper or palladium catalysts, inter alia, are employed as catalysts. In this process, the thermostatically controlled (i.e. isothermally operated) reactor and the adiabatically operated reactor, which can also be arranged in one apparatus, are connected in series, i.e. the product mixture emerging from the thermostatically controlled reactor is the educt mixture for the adiabatically operated reactor. The possibility of additionally charging the adiabatically operated reactor with nitrobenzene via a separate feed is not disclosed in this specification. In preferred embodiments, an incomplete conversion (e.g. only 70%) in the isothermally operated part is consciously accepted.

In EP 1 524 259 A1 inter alia a 2-stage process for the preparation of aromatic amines is described, in which the second process stage serves to bring the conversion to completion. In this context, an adiabatically operated reaction which contains a catalytically coated monolith as the catalyst is employed. By using this "secondary reactor" in the second stage, the service life of the "main reactor" (the first stage) can be prolonged, since complete conversion can still be achieved with the aid of the secondary reactor when the nitroaromatic has already broken through in the main reactor.

A disadvantage of the abovementioned processes is that the secondary reactor only converts the nitroaromatic into the aromatic amine if the conversion of the main reactor is not (any longer) complete. If the longest possible as complete as possible conversion in the main reactor is sought (EP 1 524 259 A1), this means that the secondary reactor remains unused for large parts of the operating time (namely the complete conversion phase of the main reactor). This leads to breakdown of valuable products by secondary reactions, which are catalyzed by the catalyst contained in the secondary reactor. If incomplete conversion is consciously accepted in the main reactor (certain embodiments of GB 1 452 466), this means that the main reactor must be overloaded, i.e. charged with more nitroaromatic than can be reacted, from the beginning. This leads to rapid deactivation of and damage to the catalyst, so that the service life is reduced and the advantage of the secondary reactor may be overcompensated. However, in the first case also, in which the main reactor is initially operated with complete conversion, at the end of the running time very high contents of unreacted nitroaromatic in the product stream of the main reactor and therefore an overloading of the secondary reactor, the catalyst of which is then rapidly deactivated, rapidly occur.

SUMMARY

It was therefore an object of the present invention to provide a process for the preparation of aromatic amines which utilizes the advantages of an at least two-stage process procedure, without having the disadvantages mentioned for the prior art (increased formation of by-products, overloading and therefore deactivation of the catalyst of the first stage).

The object has been achieved by a process for the continuous preparation of aromatic amines by hydrogenation of the corresponding nitroaromatics in the presence of catalysts arranged in reaction spaces, in which (i) an adiabatically operated reaction space RA is connected downstream of an isothermally operated reaction space RI and RA additionally also has a separate feed for the nitroaromatic to be hydrogenated, (ii) RI is fed with the nitroaromatic to be hydrogenated from the start to the end of the hydrogenation, and the product mixture emerging from RI is fed into RA from the start to the end of the hydrogenation.

wherein (iii) RA additionally, as long as the weight content of nitroaromatic measured in the product mixture emerging from RI ($\omega_{NA}$)$^{RI}$ is between 0 ppm and 5,000 ppm, is fed via the separate feed with the nitroaromatic to be hydrogenated.

DETAILED DESCRIPTION OF A PREFERRED EMBODIMENT

In this context, reaction space is understood as meaning the space in which the reaction of the nitroaromatic (or intermediate products) with hydrogen to give the desired aromatic amine takes place. The reaction space is present in a technical device for carrying out chemical reactions, the reactor. Depending on the construction, the reaction space and reactor can also be identical. The reaction space can also comprise only a part of the reactor. It is equally possible for several reaction spaces, operated isothermally and/or adiabatically, to lie within one reactor.

In the context of the present invention, isothermally means that at least the predominant part of the heat released by the reaction is removed by technical devices known to the person skilled in the art. Preferably, the heat of reaction is completely removed by technical devices.

In the context of the present invention, adiabatically accordingly means that the heat of reaction in the adiabatically operated reaction space is not removed by technical devices. In the adiabatic mode of operation, the reaction space is preferably insulated against heat losses in a particular manner. If heat losses are negligible, the reaction enthalpy is reflected quantitatively in the temperature difference between the intake and exit stream ("adiabatic jump in temperature").

Preferred reactors for the isothermally operated reaction space RI are thermostatically controlled tube or tube bundle reactors. Suitable embodiments of such reactors are described e.g. in DE-AS-2 201 528, DE-OS-2 207 166, DE-OS-198 06 810, EP-B-1 439 901, EP-A-1 569 745, EP-A-1 590 076, EP-A-1 587 612, EP-A-1 586 370, EP-A-1627 678 or DE 202 006 014 116 U1. Preferred reactors for the adiabatically operated reaction space RA are those described in DE 10 2006 035 203, paragraphs [0030] to [0033], which applies herewith as a constituent of the present disclosure. A further possible embodiment comprises a process in which the catalyst arranged in RA is present in a filter candle flowed through radially. This can be achieved, for example, by holding the catalyst in a basket constructed from two concentric, cylindrical sieve jackets with walls which are permeable to fluid. In this context, one sieve jacket has a larger radius than the other, which is also called the central tube, and the space between the sieve jackets is the reaction space. One base of this hollow cylinder is preferably completely tightly closed, while the other is closed only up to the central tube, which is open at this end. The fluid can now flow in the radial direction from the outside inwards and can then be removed through the central tube. Alternatively, the fluid can also be fed through the central tube and can then flow in the radial direction to the outside, where it is then removed. If this reaction space is in the same reactor as the isothermal reaction space, it is usually connected to the reactor outlet in a suitable manner. In a further embodiment, however, the basket can also be in an optionally widened pipeline lying downstream of the isothermal reaction space or a further reactor.

In the process according to the invention, at least one adiabatically operated reaction space is connected downstream of an isothermally operated reaction space, i.e. the process comprises at least two reaction spaces connected in series. It is possible, but not absolutely necessary, additionally to introduce fresh hydrogen or a mixture of hydrogen and inert gases into the downstream reaction spaces. The nitroaromatic fed into RA is the sum of nitroaromatic which has not reacted in RI and nitroaromatic fed in via the separate feed.

It is also conceivable to connect more than two reaction spaces in series, that is to say, for example, cascades, such as "isothermal—adiabatic—adiabatic", "isothermal—isothermal—adiabatic—adiabatic" or other combinations. Preferably a maximum of 10 reaction spaces are connected in series, particularly preferably a maximum of 5, very particularly preferably a maximum of 3, exceptionally very particularly preferably a maximum of 2. Preferably, the first reaction space of a cascade in the inwards flow direction of the nitroaromatic is operated isothermally and the last reaction space of this cascade is operated adiabatically. The invention is explained in more detail in the following by the embodiment with two reaction spaces connected in series. It is an easy matter for the person skilled in the art to apply the information to systems with more than two reaction spaces if required.

Start of the hydrogenation is understood as meaning the point in time at which the nitroaromatic and hydrogen are passed over at least one of the catalysts for the first time. The end of the hydrogenation designates the point in time at which the feed of nitroaromatics is turned off completely. In the process according to the invention, the hydrogenation is preferably carried out in the gas phase. In this context, the reaction procedure in the isothermally operated reaction space is preferably carried out as described in DE 196 51 688 A1, page 3, lines 29 to 56 and page 4, lines 6 to 16, which applies herewith as a constituent of the present disclosure. However, it is to be noted that the circulating gas steam is not cooled after passing through RI, but that this cooling serving for condensation happens only after passage through the last adiabatic reaction space.

The nitroaromatic is fed into the adiabatically operated reaction space via the separate feed preferably by atomizing the liquid nitroaromatic into an additional fresh hydrogen stream or directly into the circulating gas after RI by means of two- or one-component nozzles. Alternatively, vaporization into the fresh hydrogen and optionally superheating of the nitroaromatic, which is then added in gaseous form to the circulating gas stream, can also be carried out. In this case the heat of reaction liberated is transported away with the circulating gas stream, so that this brings about an increase in temperature. How great this can be depends decisively on the design of the pipelines and apparatuses downstream of RA and limits the amount of nitroaromatic which can be metered in between RI and RA. By the use of a common circulating gas system, the regeneration of RA takes place in the same process step as the regeneration of RI (cf. DE 196 51 688 A1, page 3, lines 40 to 45), but at a different time, since burning off of deposits in RA is carried out only when the total oxygen of the regenerating gas stream in RI is no longer consumed and reacted to give $CO_2$.

The weight content of nitroaromatic in the product mixture emerging from RI is determined analytically at regular intervals (at least every 48 hours). For this, sampling systems known from the prior art are installed in product-carrying lines or apparatuses. The analytical determination of the weight content of nitroaromatic is carried out by means of gas chromatography. The product mixture comprises the aromatic amine, water, hydrogen, where appropriate inert gases, where appropriate non-condensable gases (e.g. methane from impurities in the hydrogen) and where appropriate unreacted nitroaromatic and by-products of the reaction, such as, for example in the case of hydrogenation of nitrobenzene to give aniline, phenol, cyclohexylamine, diphenylamine, aminophenol, cyclohexanone, benzene etc.

From experience, in large-scale industrial production complete conversion of the nitroaromatic is not yet achieved directly after the start of the hydrogenation, but in general only after a start-up phase of some hours. The precise duration of the start-up phase depends on the conditions present in the individual case. In general, the start-up phase does not exceed a period of time of 12 hours. In this start-up phase the weight content of nitroaromatic in the product mixture emerging from RI is more than 5,000 ppm. Due to the catalyst arranged in RA, this residual content of nitrobenzene in the start-up phase is reduced, and in particular to values in the product mixture emerging from RA of a maximum of 2,000 ppm, preferably a maximum of 500 ppm, particularly preferably a maximum of 10 ppm.

Only when the weight content of nitroaromatic in the product mixture emerging from RI reaches or falls below 5,000 ppm (the reactor has been "run-in" for the running period) is the additional feeding in of nitroaromatic into RA started via the separate feed. The production installation is now in the main production phase, i.e. the period of time between the end of the start-up phase and the start of the end phase of the hydrogenation, i.e. the period of time towards the end of a running period in which—as a result of deactivation of the catalyst—the specific loading must be decreased stepwise. The specific loadings of nitroaromatic with which the two reaction spaces are charged are adjusted in each production phase such that the total conversion of nitroaromatic is as complete as possible, i.e. the weight content of nitroaromatic in the product mixture emerging from RA is a maximum of 1,000 ppm, preferably a maximum of 500 ppm, particularly preferably a maximum of 100 ppm, particularly preferably a maximum of 10 ppm and exceptionally particularly preferably 0 ppm. In this context, the higher values (>100 ppm to 1,000 ppm) are achieved in the start-up and end phase and the lower values (0 ppm to ≤100 ppm) are achieved in the main production phase.

In the main production phase, the specific loading ($B_{RI}$) of the isothermally operated reaction space with nitroaromatic is in the range between 0.20 $kg_{nitroaromatic}/(1_{catalyst} \cdot h)$ and 5.00 $kg_{nitroaromatic}/(1_{catalyst} \cdot h)$, preferably in the range between 0.50 $kg_{nitroaromatic}/(1_{catalyst} \cdot h)$ and 3.00 $kg_{nitroaromatic}/(1_{catalyst} \cdot h)$, particularly preferably in the range between 0.60 $kg_{nitroaromatic}/(1_{catalyst} \cdot h)$ and 1.50 $kg_{nitroaromatic}/(1_{catalyst} \cdot h)$. In the start-up phase, $B_{RI}$ is increased stepwise from zero to the desired value, and in the end phase it is decreased stepwise from the particular value to zero.

In the main production phase, the specific loading of the adiabatically operated reaction space via the separate feed $(B_{RA})^{sep.}$ is in the range between 0.020 $kg_{nitroaromatic}/(1_{catalyst} \cdot h)$ and 0.500 $kg_{nitroaromatic}/(1_{catalyst} \cdot h)$, preferably in the range between 0.050 $kg_{nitroaromatic}/(1_{catalyst} \cdot h)$ and 0.300 $kg_{nitroaromatic}/(1_{catalyst} \cdot h)$, particularly preferably in the range between 0.100 $kg_{nitroaromatic}/(1_{catalyst} \cdot h)$ and 0.200 $kg_{nitroaromatic}/(1_{catalyst} \cdot h)$. In the start-up phase, $(B_{RA})^{sep.}$ is zero, and it is increased stepwise to the desired value at the start of the main production phase. In the end phase, $(B_{RA})^{sep.}$ is decreased stepwise from the particular value to zero.

The weight content of nitroaromatic in the product mixture emerging from RI or RA can be determined analytically by means of gas chromatography. Suitable methods for this are sufficiently known to the person skilled in the art. In addition, it is an easy matter for the person skilled in the art to establish, via the reaction enthalpy of the hydrogenation and the heat capacity of the medium, a correlation between the adiabatic jump in temperature, which in RA (that is to say the difference between the product exit temperature and the temperature of the educt mixture before contact with the catalyst present in RA), and the known amounts of nitroaromatic fed into RA (that is to say the sum of unreacted nitroaromatic from RI and nitroaromatic additionally fed in via the separate feed) such that the weight content of nitroaromatic in the product mixture emerging from RA can be calculated. Conversely, by analytical determination of the weight content of nitroaromatic emerging from RA, the content of unreacted nitroaromatic from RI can be concluded via the adiabatic jump in temperature and the amount of nitroaromatic additionally fed in. An increase in the temperature of the product mixture emerging from RA is often a first indication of an inadequate conversion in the isothermally operated reaction space. A temperature of the product mixture emerging from RA which is constant within narrow limits, on the other hand, is an indication of a satisfactory reaction procedure, which can be controlled such that the total conversion is as complete as possible (see above).

As soon as the weight content of nitroaromatic in the product mixture emerging from RI reaches such high values that an overloading of the secondary reactor (and therefore too high weight contents of nitroaromatic in the product mixture emerging from RA) is to be feared, the specific loading of the adiabatically operated reaction space via the separate feed $(B_{RA})^{sep.}$ is reduced stepwise to 0 and the reaction is continued until a satisfactory conversion is also no longer achieved with the adiabatically operated reaction space. Preferably, the reduction in the separate feed of nitroaromatic for the adiabatically operated reaction space is carried out to the extent in which unreacted nitroaromatic emerges from RI. As explained above, the temperature of the product stream emerging from RA can serve as an indication of this. Due to the nitroaromatic breaking through, the adiabatic jump in temperature would increase if the amount of educts metered in were to remain constant. Concretely, in this context in the preferred procedure as soon as $(\omega_{NA})^{RI}$ increases from values in the range between 0 ppm and 1,000 ppm to values above 1,000 ppm, the amount of nitroaromatic fed into RA via the separate feed per liter of catalyst and hour $(=(B_{RA})^{sep.})$ is reduced stepwise such that the temperature of the product mixture emerging from RA remains constant in the range of ±10 K, preferably in the range of ±5 K, particularly preferably in the range of ±2 K. The hydrogenation is then preferably continued further until the content of nitroaromatic in the product also reaches a level which is no longer acceptable downstream of the adiabatically operated reaction space. Preferably, the hydrogenation is ended as soon as the weight content of nitroaromatic determined in the product mixture emerging from RA $(\omega_{NA})^{RA}$ increases from values in the range between 0 ppm and 1,000 ppm to values above 1,000 ppm. In the context of this invention, the term "liter of catalyst" always relates to the bulk volume of the catalyst.

Suitable catalysts for the isothermally operated reaction space are in principle all the hydrogenation catalysts known to the person skilled in the art. Preferably, multi-component supported catalysts as described in EP-A-0 011 090 page 5, line 10 to page 8, line 5 are employed. This section of text applies herewith as a constituent of the present disclosure.

Suitable catalysts for the adiabatically operated reaction space are in principle all the hydrogenation catalysts known to the person skilled in the art. Multi-component supported catalysts in suitable holding devices are preferably used. Due to the low pressure loss, suitable catalysts are e.g. those applied to monolithic supports as described in EP 1 524 259 A1, page 5, Example 1, which applies herewith as a constituent of the present disclosure. Catalysts which are supported on knitted wire fabrics (i.e. on mesh fabrics produced from wires or metal threads) are particularly preferably used. The knitted wire fabrics are produced with wire processing machines which are known per se, such as are usual, for example, for uses in the automobile industry, process engineering and environmental engineering (e.g. wire knitting machines). In this embodiment, the invention accordingly relates to a process in which the catalyst arranged in RA contains catalytically active components on a knitted wire fabric, and in which the catalytically active components comprise at least:

(a) 1-100 g/l$_{support}$ of at least one metal of groups 8 to 12 of the periodic table of the elements, and (b) 0-100 g/l$_{support}$ of at least one transition metal of groups 4 to 6 and 12 of the periodic table of the elements, and (c) 0-100 g/l$_{support}$ of at least one metal of the main group elements of groups 14 and 15 of the periodic table of the elements.

By the process according to the invention, not only can the service life of the isothermally operated reaction space (RI) be increased, the adiabatically operated reaction space can also be utilized to the optimum, since before the point in time at which the conversion in RI is no longer complete, it already hydrogenates the nitroaromatic to give the aromatic amine under controlled conditions, i.e. without overloading. The process is particularly suitable for extending the production capacity of existing isothermally operating installations, since the isothermally operated reactors of expensive construction do not have to be de-installed. In particular, the process according to the invention is suitable for the preparation of aniline by hydrogenation of nitrobenzene.

Example 1

One liter of an α-Al$_2$O$_3$ support in the form of spheres with a diameter of 3 to 5 mm, a BET surface area of 9.8 m$^2$/g, an absorbency of 45.1 ml of water per 100 g of support and a bulk density of 812 g/l was impregnated with 366 ml of an aqueous solution containing 10.8 g of NaOH. The solution was absorbed completely by the support within a few minutes.

The damp support was dried in a hot ascending strong stream of air. The drying time to constant weight was approximately 15 minutes. The residual moisture content after cooling was about 1% of the absorbency of the support.

The support pretreated in this way was impregnated according to its absorbency with 366 ml of an aqueous sodium tetrachloropalladate solution which contained 9 g of palladium, and left to stand for 15 minutes. For reduction of the palladium compound deposited on the support to metallic palladium, the catalyst was covered with a layer of 400 ml of a 10% strength aqueous hydrazine hydrate solution and left to stand for 2 hours. Thereafter, the catalyst was washed thoroughly with completely desalinated water until ions of the compounds used in the preparation of the catalyst were no longer detectable in the wash water, which was the case after approx. 10 hours.

Drying was then again carried out to constant weight in a strong hot ascending stream of air. The Pd-containing catalyst was then impregnated with 366 ml of an aqueous solution containing 9 g of vanadium as vanadyl oxalate. Drying of the support in the stream of hot air was carried out as described above. The catalyst was then heat-treated in a tubular oven at 300° C. for 6 hours, whereby the oxalate decomposed.

Finally, the catalyst was impregnated with 366 ml of an aqueous solution containing 3 g of lead in the form of lead acetate and dried again in an ascending stream of air.

The finished catalyst contained 9 g of palladium, 9 g of vanadium and 3 g of lead and corresponded to the catalyst from DE 2849002.

Example 2

Comparison Example

A 285 cm high heap of a catalyst prepared according to Example 1 was introduced into a reactor tube thermostatically controlled with oil (isothermally operated reaction space) with an internal diameter of approx. 26 mm. The catalyst was flushed first with nitrogen and then with hydrogen and was subsequently heated up to 240° C. in a stream of hydrogen of approx. 1,570 l/h in the course of 5 hours. Evaporation of nitrobenzene in the stream of hydrogen was then started. The specific loading was increased stepwise to 1.02 kg$_{nitrobenzene}$/(1$_{catalyst}$·h), it being ensured that the temperature in the reaction tube did not rise above 450° C. at any point. On average over time, the specific loading was therefore 1.00 kg$_{nitrobenzene}$/(1$_{catalyst}$·h). The temperature in the catalyst heap (and therefore the position of the reaction front) was monitored, and towards the end of the reaction, from approx. 700 hours, the oil temperature was increased stepwise from 240° C. to 300° C., so that complete conversion was achieved for as long as possible. After 1,020 h, more than 1,000 ppm by weight of nitrobenzene were to be detected in the reaction product and the reaction was ended. Approx. 1,500 kg of nitrobenzene were reacted. The average selectivity was 99.0%.

Example 3

Example According to the Invention

In addition to the experimental set-up in Example 2, an adiabatically operated reactor (adiabatically operated reaction space, "secondary reactor") was connected downstream of the thermostatically controlled tube reactor. This had a volume of 250 ml and was charged with a catalyst supported on a knitted wire fabric. The catalytically active coating of the knitted fabric comprised approx. 75 g/l of aluminium oxide and 4 g/l each of palladium and vanadium, which were applied successively. A separate feed of nitrobenzene and hydrogen into the product stream was provided between the two reactors.

The reactors were flushed first with nitrogen and then with hydrogen and were subsequently heated up to 240° C. in a stream of hydrogen of approx. 1,570 Nl/h in the course of 5 hours. Evaporation of nitrobenzene in the stream of hydrogen was then started. The specific loading was increased stepwise to 1.02 kg$_{nitrobenzene}$/(1$_{catalyst}$·h), it being ensured that the temperature in the reaction tube did not rise above 450° C. at any point.

At the same time, 90 g/h of nitrobenzene and 50 l/h of hydrogen were metered in between the main reactor and the secondary reactor via the separate feed.

The temperature in the catalyst heap of the isothermally operated reaction space ("main reactor")—and therefore the position of the reaction front—was monitored, and towards the end of the reaction, from approx. 700 hours, the oil temperature was increased stepwise from 240° C. to 300° C., so that complete conversion was achieved in the main reactor for as long as possible. After about 1,000 h, the nitrobenzene content in the product exit of the isothermally operated reaction space rose to values of >1,000 ppm by weight. From this point in time the loading of the secondary reactor was lowered slowly to 0 kg$_{nitrobenzene}$/(1$_{catalyst}$·h), so that the product exit temperature was kept constant within a range of ±2 K. After 1,080 h, the nitrobenzene content in the product exit of the adiabatically operated reaction space also rose to values of >1,000 ppm by weight and the reaction was ended. In total, in this way in this cycle approx. 1,600 kg of nitrobenzene were reacted in the main reactor and approx. 95 kg of nitrobenzene were reacted in the secondary reactor, that is to say in total approx. 1,695 kg of nitrobenzene. It was thus possible both to improve the utilization of the main reactor and to react an increased amount of nitrobenzene during the complete conversion phase in this experimental set-up.

The invention claimed is:

1. A process for preparing an aromatic amine by hydrogenation of a corresponding nitroaromatic in the presence of a catalyst arranged in a reaction space, said process comprising
   (i) connecting an adiabatically operated reaction space RA downstream of an isothermally operated reaction space RI and wherein RA additionally also comprises a separate feed for the nitroaromatic to be hydrogenated,
   (ii) feeding RI with the nitroaromatic to be hydrogenated from start to end of hydrogenation, and wherein product mixture emerging from RI is fed into RA from start to end of hydrogenation,
   wherein
   (iii) as long as weight content of nitroaromatic measured in product mixture emerging from RI $(\omega_{NA})^{RI}$ is from 0 ppm to 5,000 ppm, RA is additionally fed via a separate feed with the nitroaromatic to be hydrogenated.

2. The process according to claim 1, wherein as soon as $(\omega_{NA})^{RI}$ increases from a value in a range from 0 ppm to 1,000 ppm to a value above 1,000 ppm, the amount of nitroaromatic fed into RA via the separate feed per liter of catalyst per hour is reduced stepwise such that temperature of product mixture emerging from RA remains constant in a range of ±10 K.

3. The process according to claim 1, in which hydrogenation is ended as soon as weight content of nitroaromatic determined in the product mixture emerging from RA $(\omega_{NA})^{RA}$ increases from a value in a range from 0 ppm to 1,000 ppm to a value above 1,000 ppm.

4. The process according to claim 1, in which catalyst arranged in RA comprises a catalytically active component on a knitted wire fabric, and in which the catalytically active component comprises at least:
   (a) 1-100 $g/l_{support}$ of at least one metal of groups 8 to 12 of the periodic table of the elements, and
   (b) 0-100 $g/l_{support}$ of at least one transition metal of groups 4 to 6 and 12 of the periodic table of the elements, and
   (c) 0-100 $g/l_{support}$ of at least one metal of the main group elements of groups 14 and 15 of the periodic table of the elements.

5. The process according to claim 1, in which catalyst arranged in RA is present in a filter candle flowed through radially.

6. The process according to claim 1, in which nitrobenzene is employed as the nitroaromatic.

* * * * *